(12) United States Patent
Shafirstein et al.

(10) Patent No.: US 7,361,173 B2
(45) Date of Patent: *Apr. 22, 2008

(54) CONDUCTIVE INTERSTITIAL THERMAL THERAPY DEVICE

(75) Inventors: Gal Shafirstein, Little Rock, AR (US); Scott L. Ferguson, Vilonia, AR (US); Milton Waner, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 444 days.

This patent is subject to a terminal disclaimer.

(21) Appl. No.: 11/028,157

(22) Filed: Jan. 3, 2005

(65) Prior Publication Data

US 2005/0119645 A1 Jun. 2, 2005

Related U.S. Application Data

(63) Continuation of application No. 10/336,973, filed on Jan. 6, 2003, now Pat. No. 6,872,203, which is a continuation-in-part of application No. 10/228,482, filed on Aug. 27, 2002, now Pat. No. 6,780,177.

(51) Int. Cl.
*A61B 18/18* (2006.01)
(52) U.S. Cl. .......................... 606/28; 606/15
(58) Field of Classification Search .............. 606/7, 606/13–16, 27–31, 41; 607/88, 89
See application file for complete search history.

(56) References Cited

U.S. PATENT DOCUMENTS 4,646,737 A * 3/1987 Hussein et al. ............... 606/28
4,672,962 A    6/1987 Hershenson
4,691,703 A    9/1987 Auth et al.
4,753,201 A    6/1988 Fukuo et al.
4,860,744 A    8/1989 Johnson et al.
4,872,458 A   10/1989 Kanehira et al.

(Continued)

OTHER PUBLICATIONS

Neuwirth, R., et al., The Endometrial Ablator: A New Instrument, Obstetrics & Gynecology, vol. 83, No. 5, Part 1, pp. 792-796, May 1994.

(Continued)

*Primary Examiner*—Michael Peffley
(74) *Attorney, Agent, or Firm*—Ray F. Cox, Jr.

(57) ABSTRACT

An apparatus and method for thermally destroying tumors in which heat is generated by electrical resistance heating conducted to the target tissue. Computerized scanning is used to optimize the geometry of a thermal probe. The probe has a metal tip heated by a remote laser. The metal tip is mounted on the end of a wave guide fiber for transmitting the laser radiation to the metal tip. The tip is coated with a thin layer of biocompatible ceramic to avoid coagulated tissue sticking to the tip. The tip has one or more thin, thermally-conductive elements which deploy in stages to coagulate the tumor. The conductive elements may be thin wires or blades. On one embodiment, the conductive elements are composed of a shape memory material that is folded against the tip at lower temperatures and deploys at selected higher temperatures. In another embodiment, the conductive elements are blades that are deployed mechanically. The tip may be provided with a miniature thermocouple to provide temperature feedback information.

5 Claims, 7 Drawing Sheets

U.S. PATENT DOCUMENTS

| | | |
|---|---|---|
| 4,949,718 A | 8/1990 | Neuwirth et al. |
| 5,047,025 A | 9/1991 | Taylor et al. |
| 5,057,105 A | 10/1991 | Malone et al. |
| 5,105,808 A | 4/1992 | Neuwirth et al. |
| 5,159,925 A | 11/1992 | Neuwirth et al. |
| 5,190,539 A | 3/1993 | Fletcher et al. |
| 5,191,883 A | 3/1993 | Lennox et al. |
| 5,292,321 A * | 3/1994 | Lee .................. 606/28 |
| 5,345,936 A | 9/1994 | Pomeranz et al. |
| 5,417,689 A * | 5/1995 | Fine .................. 606/41 |
| 5,425,731 A | 6/1995 | Daniel et al. |
| 5,456,682 A | 10/1995 | Edwards et al. |
| 5,492,529 A | 2/1996 | Neuwirth et al. |
| 5,536,267 A * | 7/1996 | Edwards et al. ........ 606/41 |
| RE35,330 E | 9/1996 | Malone et al. |
| 5,571,153 A | 11/1996 | Wallsten |
| 5,586,982 A | 12/1996 | Abela |
| 5,672,173 A | 9/1997 | Gough et al. |
| 5,683,384 A * | 11/1997 | Gough et al. .......... 606/41 |
| 5,810,802 A | 9/1998 | Panescu et al. |
| 5,827,269 A * | 10/1998 | Saadat .................. 606/28 |
| 5,860,974 A | 1/1999 | Abele |
| 5,868,740 A | 2/1999 | LeVeen et al. |
| 5,891,134 A | 4/1999 | Goble et al. |
| 5,897,552 A | 4/1999 | Edwards et al. |
| 5,957,920 A | 9/1999 | Baker |
| 6,024,743 A | 2/2000 | Edwards |
| 6,053,912 A | 4/2000 | Panescu et al. |
| 6,056,746 A | 5/2000 | Goble et al. |
| 6,071,280 A | 6/2000 | Edwards et al. |
| 6,139,570 A | 10/2000 | Saadat et al. |
| 6,221,071 B1 | 4/2001 | Sherry et al. |
| 6,238,392 B1 * | 5/2001 | Long .................. 606/41 |
| 6,258,086 B1 | 7/2001 | Ashley et al. |
| 6,290,697 B1 | 9/2001 | Tu et al. |
| 6,293,943 B1 | 9/2001 | Panescu et al. |
| 6,312,428 B1 | 11/2001 | Eggers et al. |
| 6,689,127 B1 * | 2/2004 | Gough et al. .......... 606/41 |
| 6,706,037 B2 | 3/2004 | Zvuloni |
| 6,780,177 B2 | 8/2004 | Shafirstein et al. |
| 6,872,203 B2 | 3/2005 | Shafirstein |
| 7,182,761 B2 * | 2/2007 | Garabedian et al. ........ 606/41 |
| 2004/0204683 A1 | 10/2004 | McGuckin, Jr. et al. |
| 2006/0167445 A1 | 7/2006 | Shafirstein |

OTHER PUBLICATIONS

Written Opinion, IPEA, PCT/US03/20474, Apr. 23, 2004.
International Preliminary Examination Report, IPEA, PCT/US03/20474, Aug. 18, 2004.
International Search Report and Written Opinion of International Searching Authority, PCT/US07/03426, Nov. 5, 2007.

* cited by examiner

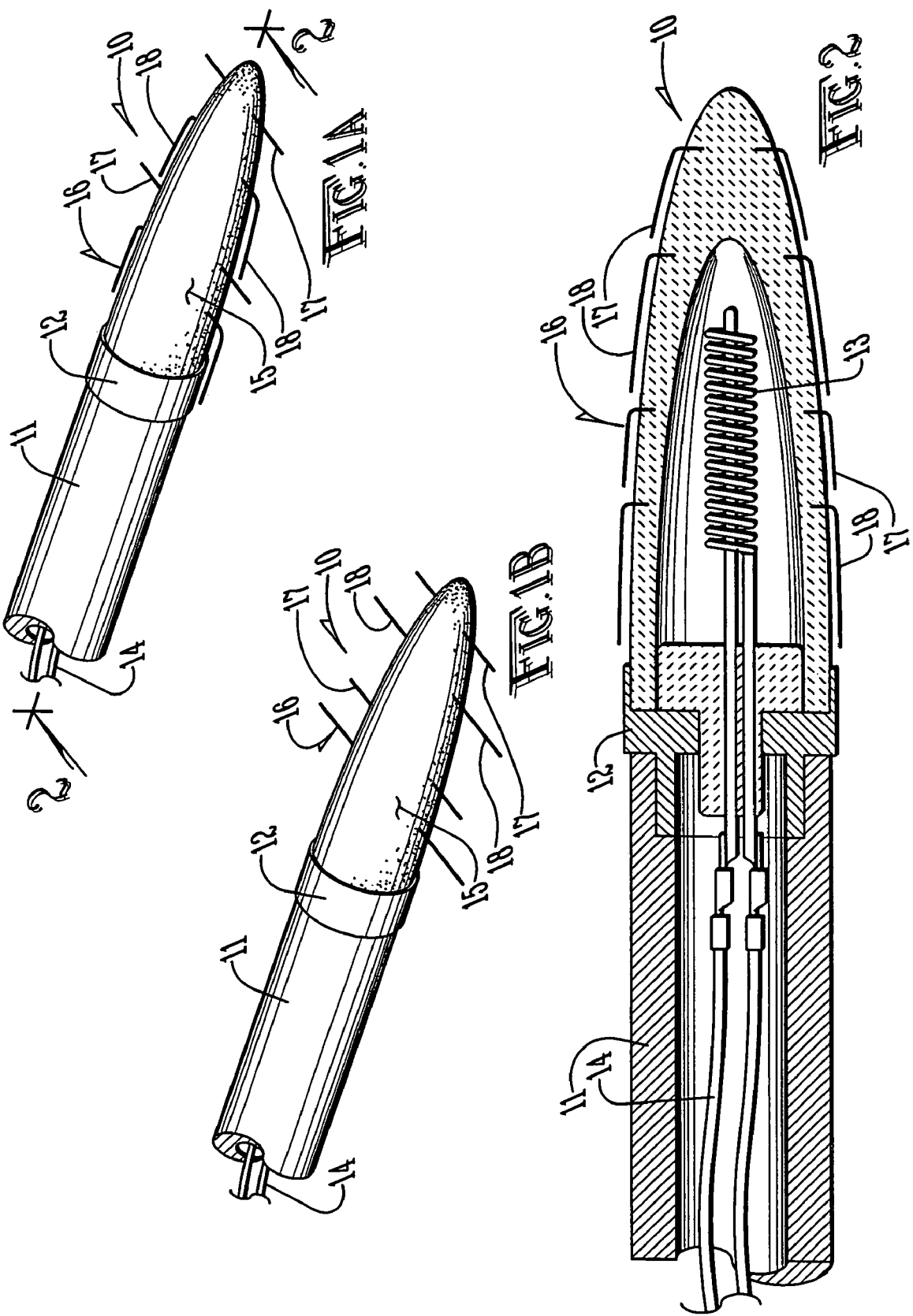

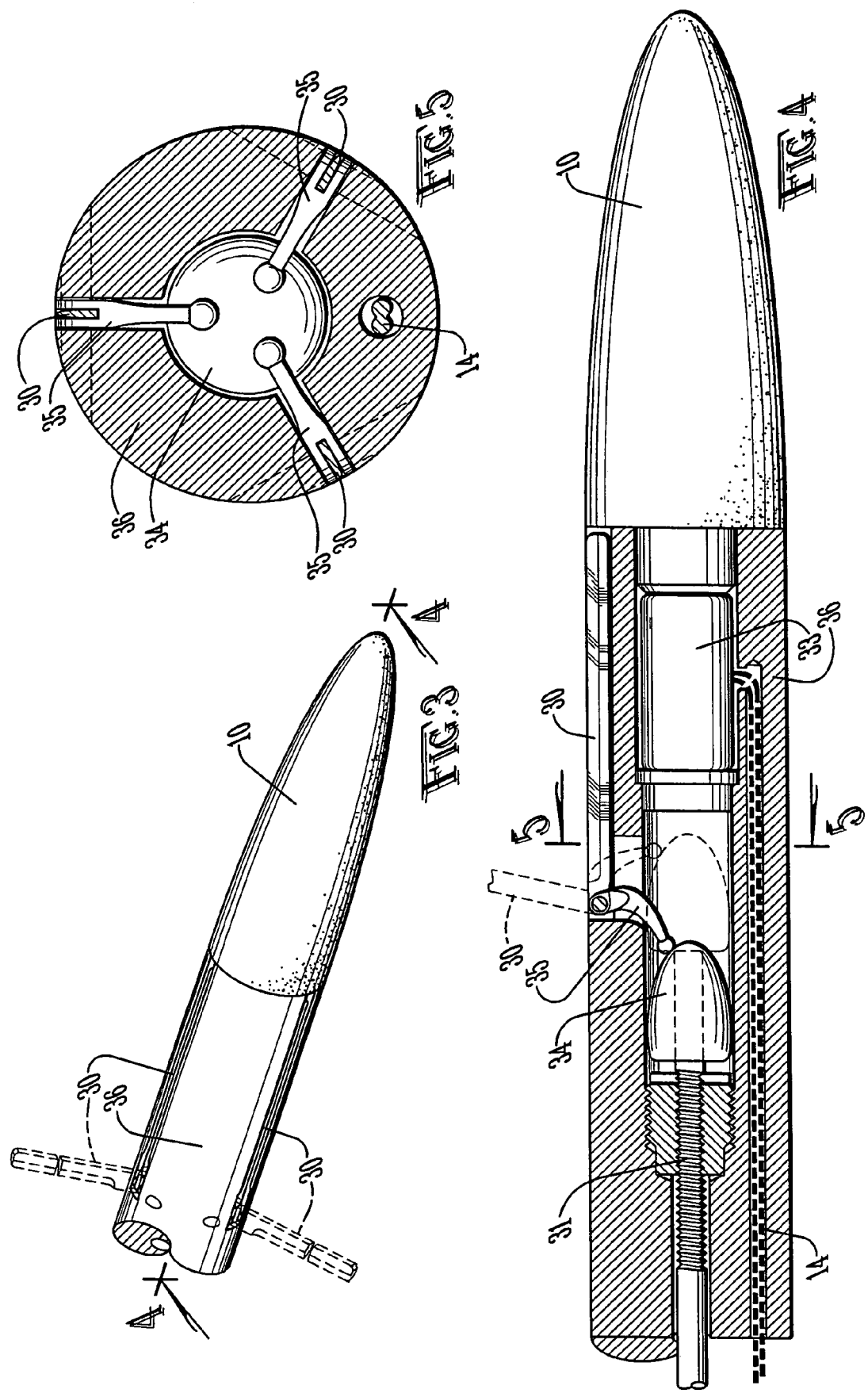

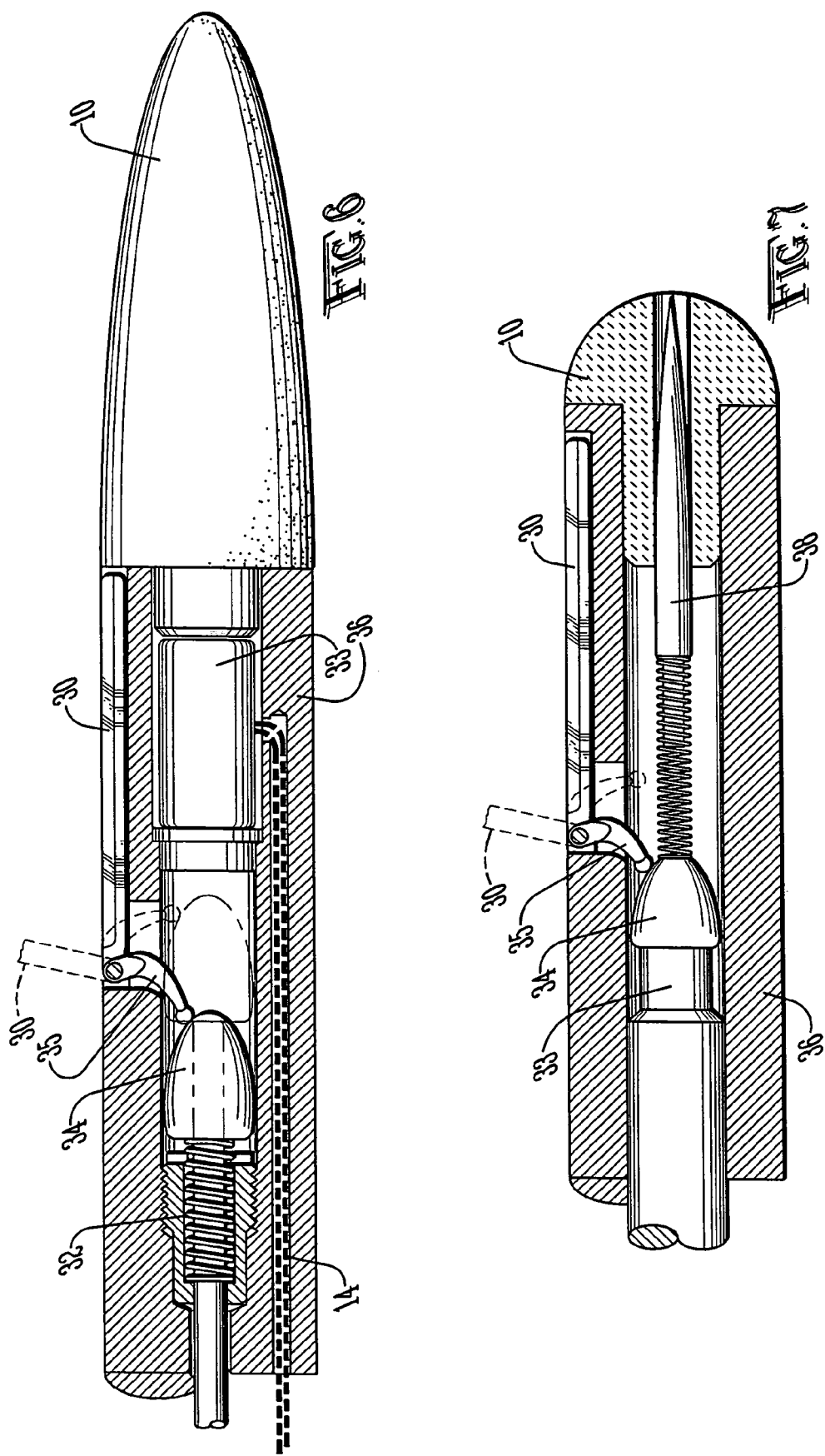

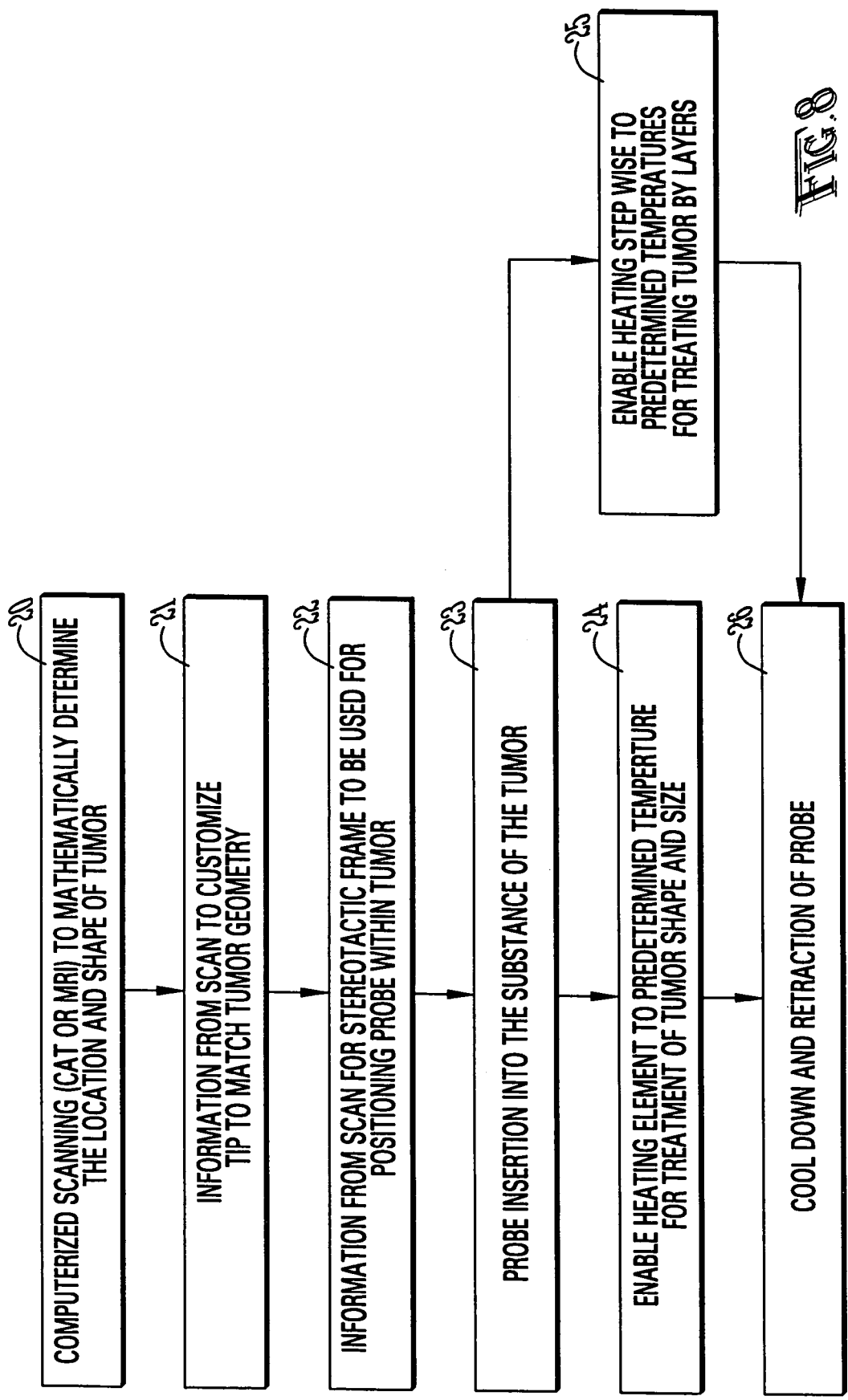

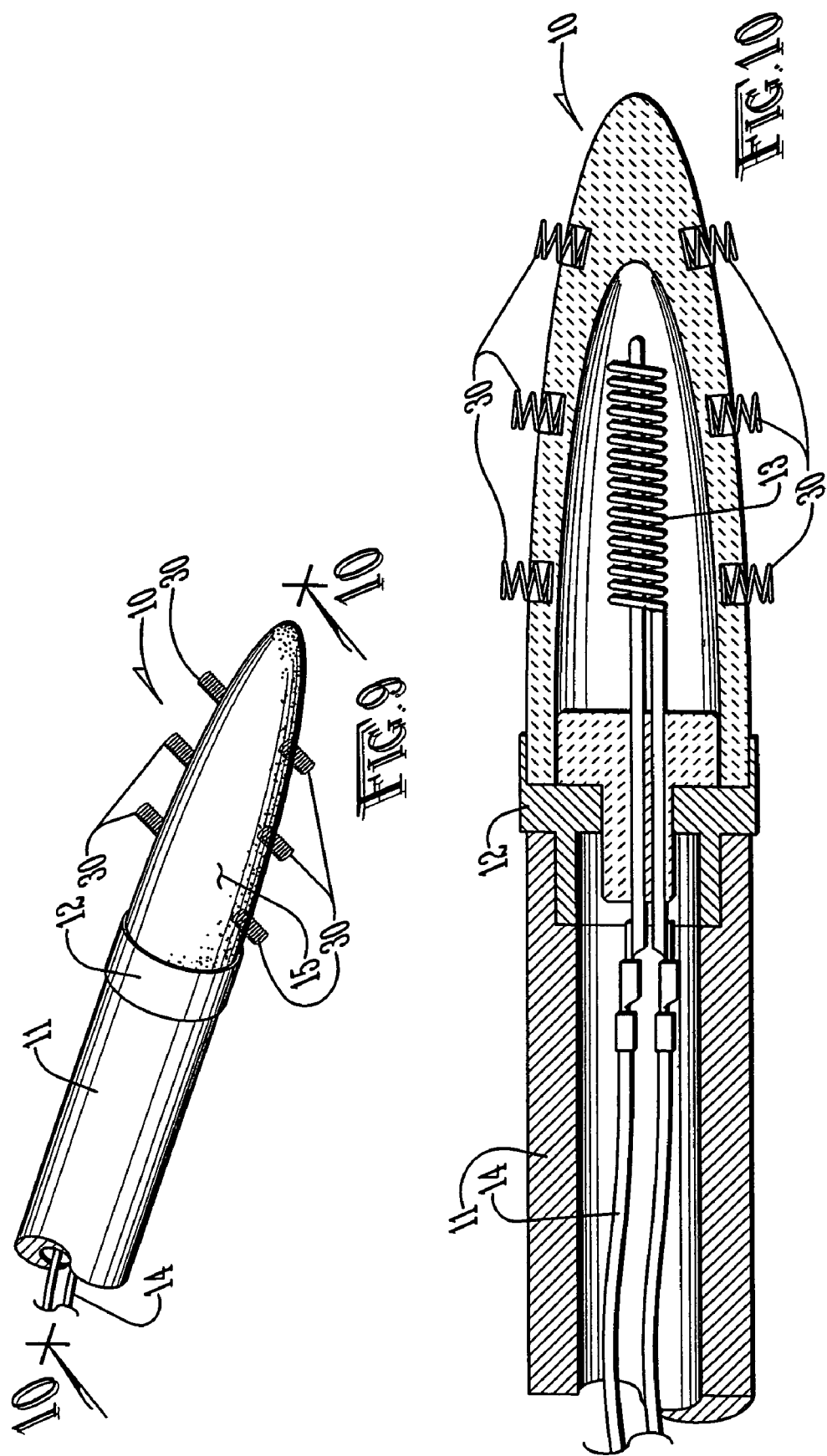

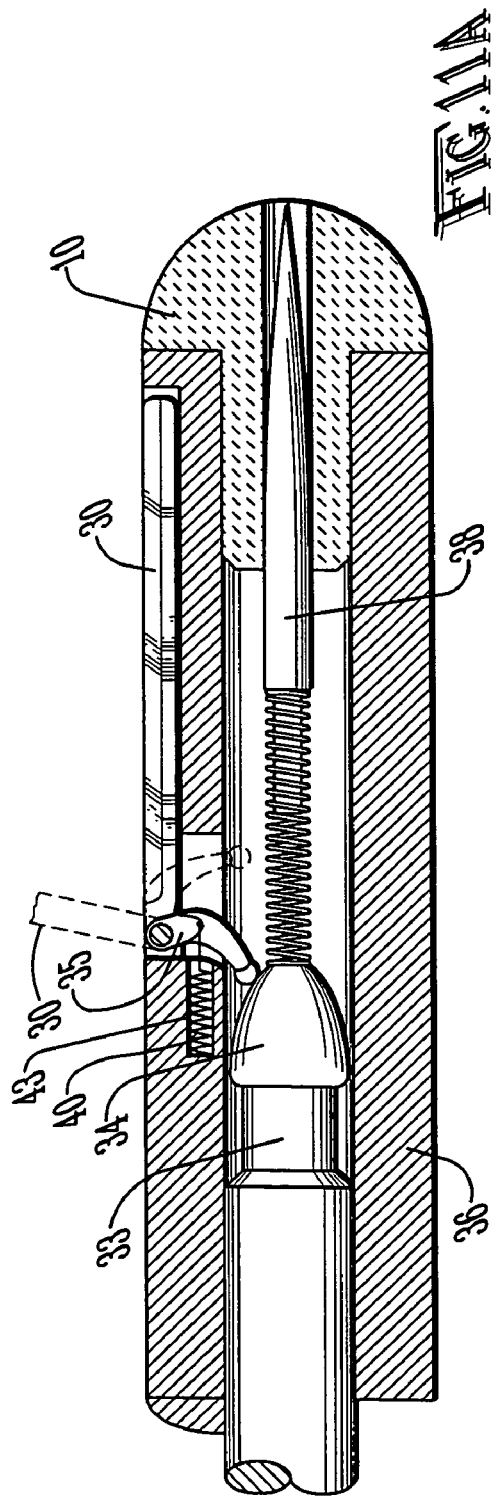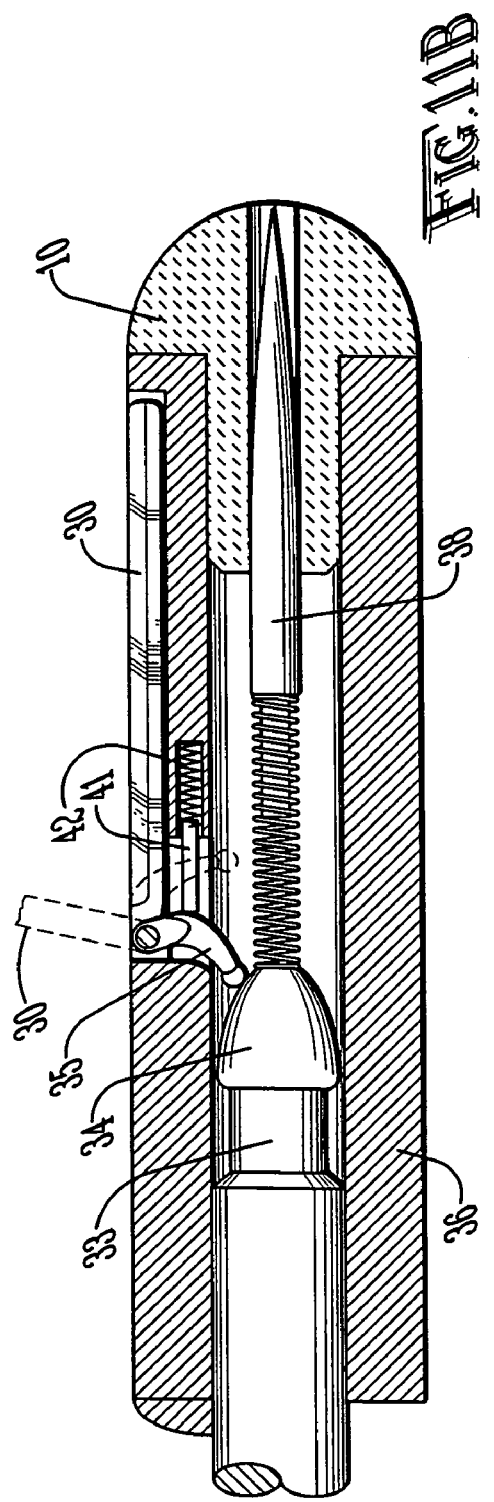

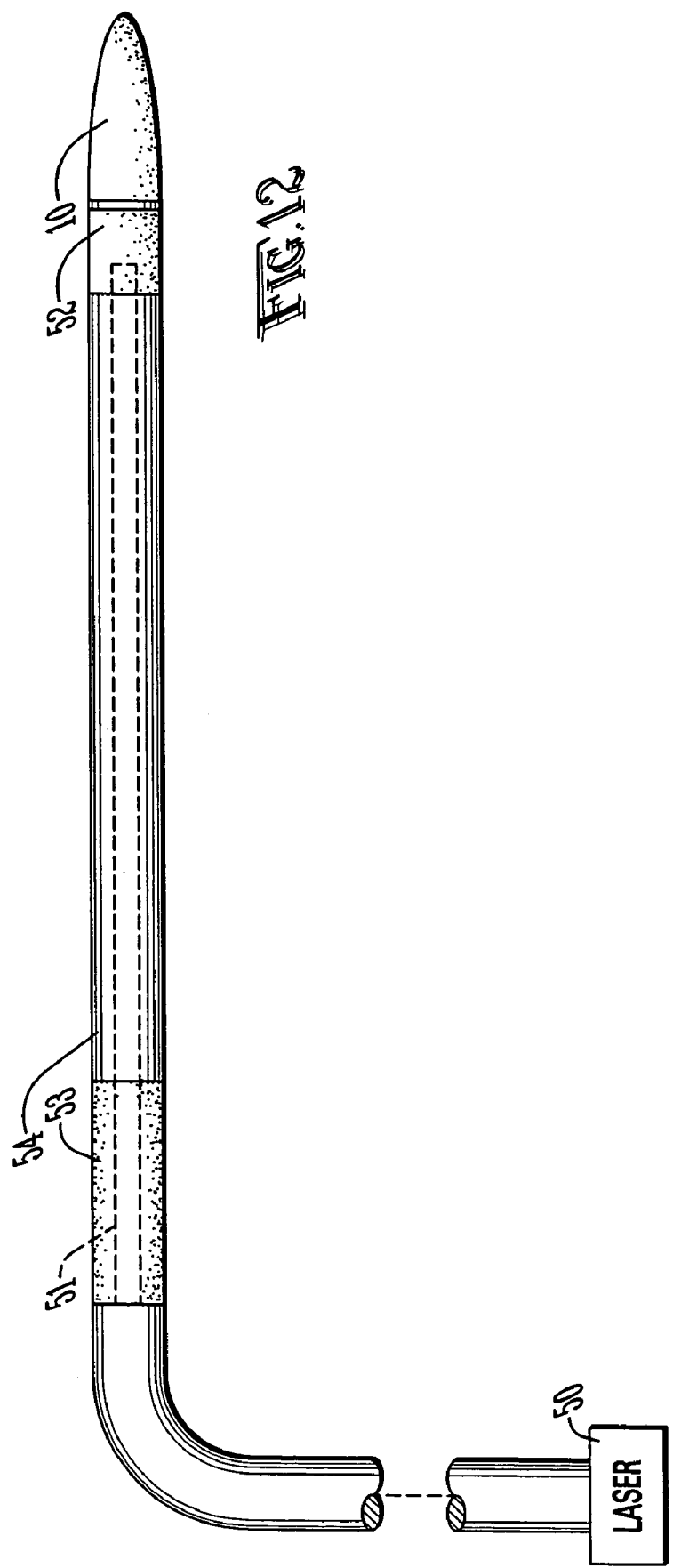

CONDUCTIVE INTERSTITIAL THERMAL THERAPY DEVICE

CROSS-REFERENCE TO RELATED APPLICATIONS

This application is a continuation of U.S. patent application Ser. No. 10/336,973 filed Jan. 6, 2003, now U.S. Pat. No. 6,872,203, which is a continuation-in-part of U.S. patent application Ser. No. 10/228,482 filed Aug. 27, 2002, now U.S. Pat. No. 6,780,177, all of which are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to methods and devices for treating body tissues such as tumors or lesions with thermal energy, and in particular, to such methods and devices that deploy thermally conductive elements to treat a predetermined shape of tissue.

2. Brief Description of the Related Art

Within the last ten years, interstitial thermal therapy of tumors has become an accepted method for treating cancerous tumors. These minimally invasive therapeutic procedures are used to kill cancer tumors without damaging healthy tissues surrounding it. Increasing the temperature of the tumor above a threshold level of about 70-130 C will cause tumor death. Interstitial thermal devices for thermal tissue ablation including radio frequency ablation (RFA), microwave and laser based technologies have been developed and have received 510K FDA clearance. All of these techniques use radiation to transfer the energy to the tumor, and therefore the heat in the tumor is generated indirectly through local energy absorption sites (e.g., blood in the case of a laser or fat in the case of RFA) could result in a non-homogenous heating of the tumor. The consequences of a non-uniform heating of the tumor could include incomplete death of the tumor and/or skin burns and injury of healthy tissues or organs. Incomplete tumor death will result in recurrence of multiple small tumors in the treated area.

Moreover, as most of the heat is transfer by radiation (in laser, RFA and microwave), it is very difficult to calculate the temperature distribution without precisely knowing the fine microstructure (down to the cell level) that cannot be predetermined with a non-invasive method. In addition the temperature measurements are also challenging; in these cases, since the probes could be directly heated by the energy sources and will show it's own temperature rather than that of the tissue. For example, in laser or RFA thermocouples may get hot from the source much quicker than tissue (as they absorb RF and laser energy more than tissue) and will show temperatures that are higher than the actual temperature in the lesion. That could result in insufficient heating and if the operator increases the amount of energy delivered to the tumor, an overheating may occur which will result in burning. Another limitation of RFA is that it is not MRI-compatible.

The limitations of the prior art are overcome by the present invention as described below.

BRIEF SUMMARY OF THE INVENTION

The present invention is an alternative to Laser Interstitial Thermal Therapy (LLIT) and RFA, which is used to destroy tumors or lesions through the absorption of radiation by tissue. However, as discussed above, in the LLIT and RFA processes, the temperature cannot be predicted or easily controlled due to the varying light and RF energy absorption properties of different types of tissue. In addition, RFA will interfere with implants (such as pacemakers) and the patient with such implants cannot be treated with RFA.

The present invention also destroys tumors thermally, but the heat is generated directly by electrical resistance heating conducted to the tissue rather than through the absorption of non-ionized radiation by the tissue. The process of the present invention involves computerized scanning (CAT, CT, PET, or MRI) to mathematically determine the location and shape of the tumor. The information derived from the scan allows a stereotactic frame or other technique such as ultrasound to be used to position a probe within the tumor.

The probe comprises a thermally conductive tip containing an electrical resistance heating element. The thermally conductive tip is mounted on the end of a fiber which is separated from the tip by a heat sink to avoid thermal conduction down the fiber. The fiber contains the electrical power leads and other electrical leads connecting to monitoring devices associated with the tip. The tip is coated with a thin biocompatible coating, such as diamond-like coating, ceramic, polymers and the like, to avoid coagulated tissue sticking to the tip.

The area of tissue treated by the tip is determined by the addition of one or more thin, thermal conductive elements, which may be formed of shape memory material, such as nitinol. The shape memory elements are desirably in the form of thin wires or pins which are folded against the tip at lower temperatures and which deploy at selected higher temperatures. The shape memory elements may be deployed in multiple stages at succesively higher temperatures so that succesive layers of the tumor are exposed to specific temperatures during treatment. Coagulating the tumor in successive layers is desirable to avoid hemoraging. By selecting the number, size and placement of the shape memory elements, tumors of varying sizes and shapes may be treated in a predictable, controllable fashion.

In order to control the process, the tip may also be provided with a miniature thermocouple or the like to provide temperature feedback information to control the temperature of the tip. Through knowledge of the shape and location of the tumor obtained from computerized imaging, the design of the tip and shape memory elements, and the temperature feedback information, information can be presented to the operator showing the specific progress of the treatment of a tumor and allowing predictable control of the process.

In alternative embodiments, deployable pivoted razorblades rather than thin wires are employed to conduct the thermal energy to the tumor. The razorblades are deployed mechanically rather than being deployed due to temperature dependent shape memory effects. In one embodiment, a linear actuator, comprising a threaded shaft operated by a motor, deploys the razorblade thermal conductive elements. In another embodiment, a nitinol spring is heated so as to extend and deploy the razorblade elements.

In all embodiments, a pyrolytic graphite element may be used to provide the heat source. Pyrolytic graphite has unique thermal properties in that it acts as a resistor axially but is conductive radially.

In a further embodiment, the deployable razorblades are deployed mechanically by a spring-biased copper conductor that serves a dual function—as a plunger to push deploying arms on the razorblades and also as a conductor for the power supply for the pyrolytic graphite heater element. The plunger is housed in a shaft which is coated with an electrically conductive material, for example, gold, to act as the power return or ground so as to complete the electrical circuit supplying power to the heater element. When the plunger moves forwardly to push the arms on the razorblades, it may also extend a needle which helps to hold the probe in place when the razorblades deploy.

The deployable razorblades may be deployed in stages to treat the tumor layer by layer. The deployment may be triggered at specified temperatures as measured by temperature feedback elements in the probe tip.

The present invention uses thermal conduction, as opposed to radiation absorption, to heat the tumor/lesion volume. Since the thermal properties of tissue are relatively homogenous, the results can be predicted. The shape of the probe tip in the form of the deployable thermal conductive elements may be altered during treatment. The combination of shape and activation temperature can be predetermined for any specific tumor/lesion geometry. This offers the following advantages: highly predictable temperature distribution; larger areas can be effectively treated, in a controlled manner, since the heat is dissipated primarily by conduction; localized carbonization will not result in tunneling and the process is safer than LLIT or RFA; the maximum temperature in the treatment zone will never exceed the temperature at the tip of the probe, and therefore, one can easily control the maximum temperature within the tumor/lesion and adjacent tissues; temperature may be actively controlled via closed loop feedback system, where the maximum temperatures are measured during the process by placing miniature thermocouples at the end of the thermal probe.

These and other features, objects and advantages of the present invention will become better understood from a consideration of the following detailed description of the preferred embodiments and appended claims in conjunction with the drawings as described following.

BRIEF DESCRIPTION OF THE SEVERAL VIEWS OF THE DRAWINGS

FIGS. 1A, 1B and 2 are views of an embodiment of the present invention in which the deployable thermal conductive elements are shape memory wires. FIG. 1A is a perspective view showing the first stage deployment of the shape memory wires. FIG. 1B shows the second stage deployed. FIG. 2 is a sectional view of the device of FIGS. 1A and 1B along the lines 2-2 of FIGS. 1A and 1B with the shape memory wires in the non-deployed configuration.

FIGS. 3-5 are views of an alternative embodiment of the present invention in which the deployable thermal conductive elements are pivoted razorblades deployed by a linear actuator. FIG. 3 is a perspective view of the present invention in which the pivoted razorblades are shown by broken lines in the deployed configuration. FIG. 4 is a sectional view along the line 3-3 of FIG. 3. FIG. 5 is a sectional view along the line 5-5 of FIG. 3.

FIG. 6 is a sectional view of a further alternative embodiment of the present invention in which the deployable thermal conductive elements are pivoted razorblades deployed by a nitinol muscle wire.

FIG. 7 is a sectional view of a further alternative embodiment of the present invention in which the deployable thermal conductive elements are pivoted razorblades deployed by a plunger. The activation of the plunger also deploys a needle through the forward end of the tip.

FIG. 8 is a block diagram of the method of the present invention.

FIGS. 9 and 10 are views of an embodiment of the present invention in which the deployable thermal conductive elements are shape memory wires in the form of coils. FIG. 9 is a perspective view showing the deployment of the shape memory wires. FIG. 10 is a sectional view of the device of FIG. 9 along the lines 10-10 with the shape memory wires in the non-deployed configuration.

FIGS. 11A and 11B are sectional views of an alternative embodiment of the embodiment of FIG. 7 wherein the deployed razorblades are spring biased to aid in retraction of the razorblades from the deployed position. FIG. 11A is an embodiment in which the biasing spring is located to the proximal side of the probe and FIG. 11B is an embodiment in which the biasing spring is located to the distal side of the probe.

FIG. 12 is a schematic view of an embodiment of the invention in which the tip of the device is a metal tip heated by a remote laser through a waveguide.

DETAILED DESCRIPTION OF THE INVENTION

With reference to FIGS. 1A-10, the preferred embodiments of the present invention may be described as follows.

The present invention is a miniature thermal apparatus for the controlled destruction of malignant and benign tumors/lesions. As used herein, the terms tumors and lesions may be used interchangeably to indicate tissue to be thermally treated by the device and method of the present invention. The present invention comprises a tip 10 mounted onto a fiber 11 that can be inserted through a catheter that has been accurately placed within the tumor/lesion. The tumor/lesion is destroyed via heat generation originating from the specifically designed tip 10 that matches the tumor/lesion geometry. The tip 10 comprises a plurality of deployable thermal conductive elements that may be customized by the number, size and arrangement to be deployable into a geometry that matches the geometry of the tumor/lesion to be thermally treated. The temperature distribution around the tip 10, within the tumor/lesion and in the adjacent tissue may be predicted by mathematical models of the heat transfer equations. Software may be employed in conjunction with the mathematical models of the heat transfer to provide (1) process monitoring and control, (2) custom probe design, and (3) process simulation. Additionally, using this predictive ability, the process may be monitored and controlled with a closed loop feedback system utilizing sensors in the tip 10. The geometry of the tip 10 may be changed as a function of temperature to increase the volume of irreversibly damaged tissue in the tumor/lesion.

As shown in FIG. 8, the process of the present invention involves the step of computerized scanning (CAT, CT, PET, or MRI) to mathematically determine the location and shape of the tumor 20. The information derived from the scan allows the geometry of the tip to be customized to treat the specific shape of the tumor 21 and also allows a stereotactic frame to be used to position the probe within the tumor 22. Ultrasound or the like may be also used to position the probe. The probe is inserted into the tumor 23, and the heating element is activated to a predetermined temperature to treat the tumor 24. Alternatively, the temperature may be increased in a stepwise fashion to treat the tumor in layers 25. Finally, the probe is cooled and withdrawn from the treated tumor 26. As an adjunct to the treatment process, the coagulation of the tumor may be enhanced by the use of a drug effective in reducing bleeding from vascular damage, such as NovoSeven (recombinant factor VIIa) or other coagulant enhancement drug such as Aminocaproic acid (Amicar). NovoSeven is used to stop bleeding in various surgical procedures. The drug is delivered systemically but only works in regions of the body in which vascular damage has taken place. In the procedure of the present invention, the drug would be administered approximately ten minutes prior to the procedure. Thereafter, the apparatus of the present invention is introduced into the tumor. Once the temperature of the tissue has increased to the point that the endothelial cells in the blood vessels are damaged, coagulation is initiated by NovoSeven in the areas of the damaged vessels. The process aids in heat transfer and may aid in the destruction of the tumor by nutrient deprivation. An ancillary advantage to using NovoSeven is that it will decrease the risk of bleeding along the track of the apparatus. The drug is metabolized in about two hours.

The themally conductive tip 10 contains an electrical resistance heating element 13. The thermally conductive tip 10 is mounted on the end of fiber 11 which is separated from the tip 10 by a heat sink 12 to avoid thermal conduction down the fiber 11. The fiber 11 contains the electrical power leads 14 and may also contain other electrical leads connecting to monitoring devices associated with the tip 10. The tip 10 is coated with a thin biocompatible coating 15 to avoid coagulated tissue sticking to the tip 10. The thin biocompatible coating 15 may be diamond-like coatings, ceramic, polymers and the like.

The area of tissue treated by the tip 10 can be adjusted by the addition of one or more deployable, thermal conductive elements. The deployable elements may be shape memory elements 16 made of shape memory materials, such as nitinol. The shape memory elements 16 are desirably in the form of thin wires or pins which are folded against the tip 10 at lower temperatures as shown in FIG. 2 and which deploy at selected higher temperatures. The shape memory elements 16 may be deployed in multiple stages at succesively higher temperatures so that succesive layers of the tumor are exposed to specific temperatures during treatment. For example, a set of short shape memory elements 17 may be deployed at a first temperature and a set of longer shape memory elements 18 may be deployed at a higher second temperature. Coagulating the tumor in successive layers is desirable to avoid hemoraging. By selecting the number, size and placement of the shape memory elements 16, tumors of varying sizes and shapes may be treated in a predictable, controllable fashion.

In order to control the process, the tip 10 may also be provided with a miniature thermocouple to provide temperature feedback information to control the temperature of the tip 10. Through knowledge of the shape and location of the tumor obtained from computerized imaging, the design of the tip 10 and shape memory elements 16, and the temperature feedback information, information can be presented to the operator showing the specific progress of the treatment of a tumor and allowing predictable control of the process.

As shown in FIGS. 9 and 10, an alternative design of shape memory elements 30 employs shape memory material, such as nitinol, in the form of coils which expand to a deployed configuration as shown in FIG. 9 from a non-deployed configuration as shown in FIG. 10.

Alternative embodiments as shown in FIGS. 3-7 use deployable pivoted razorblades 30 rather than thin shape memory wires as the thermal conductive elements to conduct the thermal energy to the tumor. Desirably, the pivoted razorblades 30 may be made of biocompatible materials, such as composite materials including aluminum silicon carbide, titanium boride and the like. The pivoted razorblades 30 may be deployed mechanically rather than being deployed by a nitinol shape memory wire element. In one embodiment shown in FIG. 4, a linear actuator, comprising a threaded shaft 31 operated by a motor (not shown), deploys the razorblade 30. In another embodiment shown in FIG. 6, a nitinol spring 32 is heated so as to extend and deploy the razorblade elements 30. In both embodiments, a pyrolytic graphite element 33 may be used to provide the heat source. Pyrolytic graphite has unique thermal properties in that it acts as a resistor axially but is conductive radially.

In a further embodiment shown in FIG. 7, the deployable razorblades 30 are deployed mechanically by a spring-biased copper conductor that serves as a plunger 34 to push deploying arms 35 on the razorblades 30. The plunger 34 also acts as a conductor for the power supply for the pyrolytic graphite heater element 33. The copper conductor is housed in a shaft 36 which is coated with an electrically conductive material such as gold to act as the power return or ground so as to complete the electrical circuit supplying power to the heater element 33. When the copper conductor plunger 34 moves forwardly to push the arms 35 on the razorblades 30, it may also extend a needle 36 which helps to hold the probe in place when the razorblades 30 deploy.

FIGS. 11A and 11B are sectional views of an alternative embodiment of the embodiment of FIG. 7 wherein the deployed razorblades 30 are biased by spring 40, 42 to aid in retraction of the razorblades 30 from the deployed position. FIG. 11A is an embodiment in which biasing spring 40 is located to the proximal side of tip 10. Spring 40 is fixed at one end in a bore 43 and at the other end to deploying arm 35. As razorblade 30 is extended, spring 40 also extends and exerts a force tending to retract razorblade 30. FIG. 11B is an embodiment in which the biasing spring 42 is located to the distal side of tip 10. Spring 42 bears against pin 41 which in turn bears against deploying arm 35. As razorblade 30 is deployed, spring 42 is compressed and thereby exerts a force tending to retract razorblade 30. Biasing springs 40, 42 may also be used in the embodiments of FIGS. 4 and 6 as well as FIG. 7.

The main limitations of the present invention are that the heating process is not selective and the device may require increasing the minimum size of the catheter since the tip 10 of the probe may be larger than a standard laser tip.

These limitations are not serious, however. Even though the heating process is not selective, the device of the present invention may be used effectively to treat tumors where the surrounding area needs to be destroyed (e.g. malignant tumors). Although the size of the thermal tip 10 is expected to be larger than a standard laser tip, the maximum size could be limited to 1.6-5 mm in diameter, which is still acceptable for interstitial procedures. Also, as shown in FIG. 12, the size of the tip 10 could be reduced to LITT size, by using a laser 50 as an energy source to heat up a metal tip 10.

When using a laser 50 as an energy source, the laser 50 is remotely located from the metal tip 10 and the laser radiation is transmitted through a wave guide fiber 51 to the metal tip 10. The metal tip 10 is desirably stainless steel. The metal tip 10 absorbs the laser radiation and is heated thereby to a high temperature, e.g., 150° C. The heat of the heated metal tip 10 is dissipated to the surrounding tissue through conduction, thereby causing blood coagulation and tissue necrosis around the metal tip 10 in a well defined region. In order to limit the heat flow from the metal tip 10 to the wave guide fiber 51, a heat conductive barrier 52 in the form of insulation or a heat sink may be placed between the metal tip 10 and the wave guide fiber 51. Further, the wave guide fiber 51 may have an insulating jacket 53. The wave guide fiber 51 may also be cooled by cool air flowing through the wave guide fiber 51. A portion of the wave guide fiber 51 adjacent to the metal tip 10 may be in the form of a tube 54 through which the cool air flows. The tube 54 may be formed from a metal, such as copper, a composite material or a ceramic material.

The laser 50 is desirably a $CO_2$ laser. Although there is low absorption (around 9%) of $CO_2$ laser radiation by stainless steel, the amount of energy required to heat stainless steel is low due to the low heat capacity of stainless steel (0.46 $Jgr^{-1}C^{-1}$) compared to blood (3.6 $Jgr^{-1}C^{-1}$). Therefore, a stainless steel metal tip 10 of 1 gram could be heated to high temperatures of up to 300-500° C. by a 50 Watt $CO_2$ laser.

To avoid tissue sticking, the metal tip 10 is desirably coated with a thin layer, e.g., 5 µm, of biocompatible ceramic, such as alumina or titanium nitride, or a biocompatible polymer, such as Teflon®. A ceramic coating may be applied by physical vapor deposition, a standard process in the industry.

Since the heat of the metal tip 10 is dissipated by conduction, the temperature profile can be calculated using known finite difference or finite element methods. Since the thermal properties of all human tissues are similar, accurate temperatures predictions are possible. Since the critical temperatures are not a strong function of time, the irreversible thermal damage of tissues can be controlled through the heating time. To limit necrosis of tissues to a well defined region, the size of the metal tip 10 can be minimized. Deployable thermally conductive elements, as described heretofore, may be added to the metal tip 10 to determine the shape of the thermally treated tissue. Such deployable thermal elements may be deployed in stages.

The present invention has been described with reference to certain preferred and alternative embodiments that are intended to be exemplary only and not limiting to the full scope of the present invention as set forth in the appended claims.

The invention claimed is:

1. An apparatus for the thermal treatment of tissue, comprising:
   a heated tip having a surface; and
   deployable means connected to said tip for thermally conducting a therapeutically effective amount of thermal energy from said heated tip to the tissue;
   said deployable means, when deployed in a second configuration, having an elongated shape with a long axis disposed substantially outwardly from said heated tip;
   wherein said heated tip has a first configuration in close proximity to said surface of said heated tip and the second configuration is substantially outward from said surface of said heated tip.

2. The apparatus of claim 1 wherein said deployable means further comprises at least one second stage deployable thermally conductive element having a third configuration in close proximity to said surface of said heated tip and a fourth configuration deployed substantially outwardly from said surface of said heated tip.

3. A method for the thermal treatment of a tumor, comprising, the steps of:
   (a) imaging the tumor by a computerized scan;
   (b) utilizing the computerized scan information to provide a heated tip having deployable means for thermally conducting a therapeutically effective amount of thermal energy from said heated tip to the tumor whose deployed shape is selected to treat at least a portion of the imaged shape of the scanned tumor;
   (c) utilizing the computerized scan information for positioning the tip into the tumor;
   (d) inserting the tip into the scanned tumor;
   (e) heating the tip;
   (f) deploying the deployable means and maintaining the tip in the tumor for a sufficient period of time to substantially destroy at least a portion of the tumor; and
   (g) removing the tip from the tumor.

4. The method of claim 3 wherein the deployable means of step (b) deploy in stages at stepwise higher temperatures to treat successively larger areas of the tumor.

5. The method of claim 3 where the deployable means deploy at a predetermined temperature; and the heating of step (e) is to at least said predetermined temperature.

\* \* \* \* \*